US00PP19074P2

(12) United States Plant Patent
Horvath

(10) Patent No.: US PP19,074 P2
(45) Date of Patent: Aug. 5, 2008

(54) ***PENNISETUM ALOPECUROIDES* PLANT NAMED 'PIGLET'**

(50) Latin Name: *Pennisetum alopecuroides*
Varietal Denomination: Piglet

(76) Inventor: Brent Horvath, 10702 Seaman Rd., Hebron, IL (US) 60034

( * ) Notice: Subject to any disclaimer, the term of this patent is extended or adjusted under 35 U.S.C. 154(b) by 105 days.

(21) Appl. No.: 11/593,612

(22) Filed: Nov. 7, 2006

(51) Int. Cl.
*A01H 5/00* (2006.01)

(52) U.S. Cl. ..... Plt./384
(58) Field of Classification Search ..... None
See application file for complete search history.

(56) References Cited

U.S. PATENT DOCUMENTS

PP18,509 P3 * 2/2008 Hanna et al. ..... Plt./384

* cited by examiner

*Primary Examiner*—Wendy C. Haas
(74) *Attorney, Agent, or Firm*—Brent Horvath

(57) ABSTRACT

A new, distinct *Pennisetum alopecuroides* plant as shown and described, characterized by a short habit of 40-45 cm.

1 Drawing Sheet

Latin name: *Pennisetum alopecuroides.*
Cultivar name: 'Piglet'.

BACKGROUND OF THE INVENTION

The present invention relates to a new form of *Pennisetum alopecuroides* plant named 'Piglet'. 'Piglet' is a seedling of *Pennisetum alopecuroides* 'Hameln', not patented, characterized by a short habit of 40-45 cm, compared to the taller habit of 90 cm of the parent plant. The new plant was found as a seedling by the inventor growing in the ground in close proximity to a block of 1 gallon *Pennisetum alopecuroides* 'Hameln' in Hebron, Ill. in 1999. The selection of this plant was due to a shorter habit. Asexual, vegetative division propagation has been the only means of reproduction. Propagation has taken place at Hebron, Ill. since 2002. In 2003 we planted 60 plants in the field. To date these plants have remained uniform in height. The new *Pennisetum* has shown to be stable and identical in reproduction to the parent after making over 1550 vegetative divisions from 2002 to 2005.

SUMMARY OF THE INVENTION

In the following description, color references are made to The Royal Horticultural Society Colour Chart. The new *Pennisetum alopecuroides* plant named 'Piglet' has shown the characteristic of a short 40-45 cm habit to be unique and stable.

Plants of the new *Pennisetum* can be compared to plants of *Pennisetum alopecuroides* the species. 1. The new *Pennisetum* has a height of 40-45 cm compared to the height of *Pennisetum alopecuroides* which has a height of 100-110 cm. 2. The new *Pennisetum* has an inflorescence length of 7-8 cm compared to *Pennisetum alopecuroides* which has an the inflorescence length of 14 cm.

Plants of the new *Pennisetum* can be compared to plants of *Pennisetum alopecuroides* 'Hameln' not patented. 1. The new *Pennisetum* has a height of 40-45 cm compared to the height of *Pennisetum alopecuroides* 'Hameln' which has a height of 90 cm. 2. The new *Pennisetum* has an inflorescence length of 7-8 cm compared to *Pennisetum alopecuroides* 'Hameln' which has an the inflorescence length of 10 cm.

Plants of the new *Pennisetum* can be compared to plants of *Pennisetum alopecuroides* 'Little Bunny', not patented. 1. The new *Pennisetum* has a height of 45 cm compared to the height of *Pennisetum alopecuroides* 'Little Bunny' which has a height of 30 cm. 2. The new *Pennisetum* has an inflorescence length of 7-8 cm compared to *Pennisetum alopecuroides* 'Little Bunny' which has an the inflorescence length of 3 cm.

DESCRIPTION OF PHOTOGRAPHS

DETAILED BOTANICAL DESCRIPTION

Figure 1:
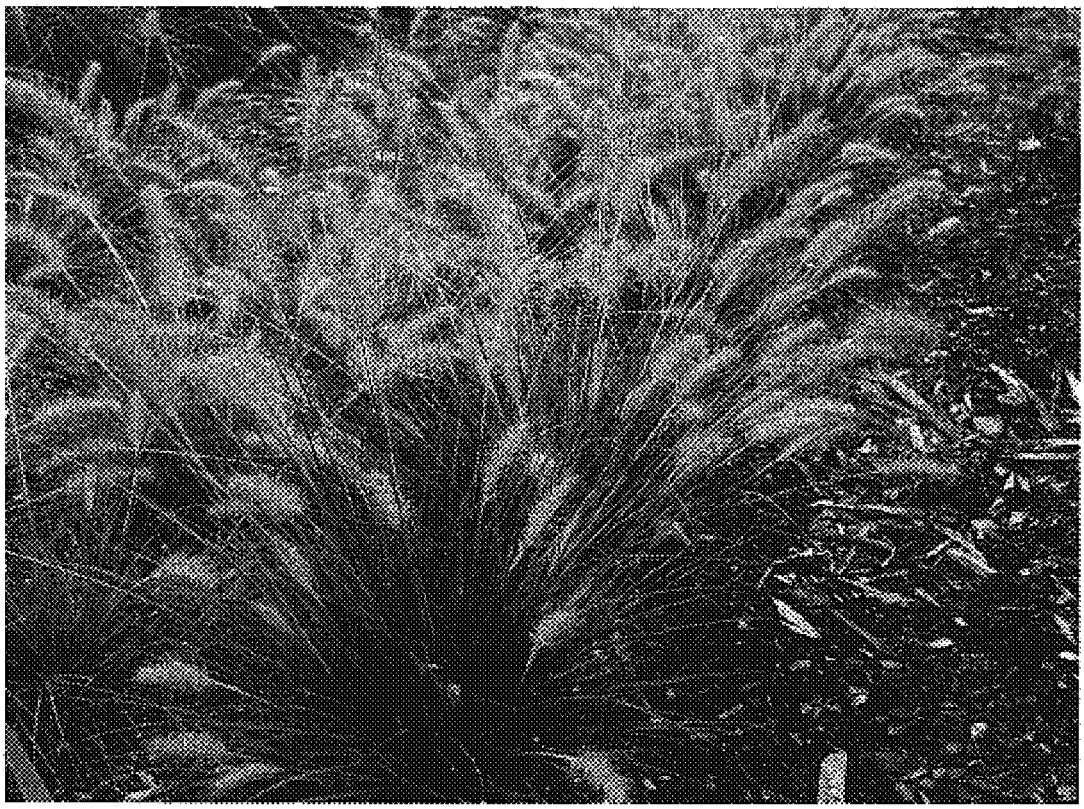
FIG. 1 shows 'Piglet' plants in the field.
Figure 2:
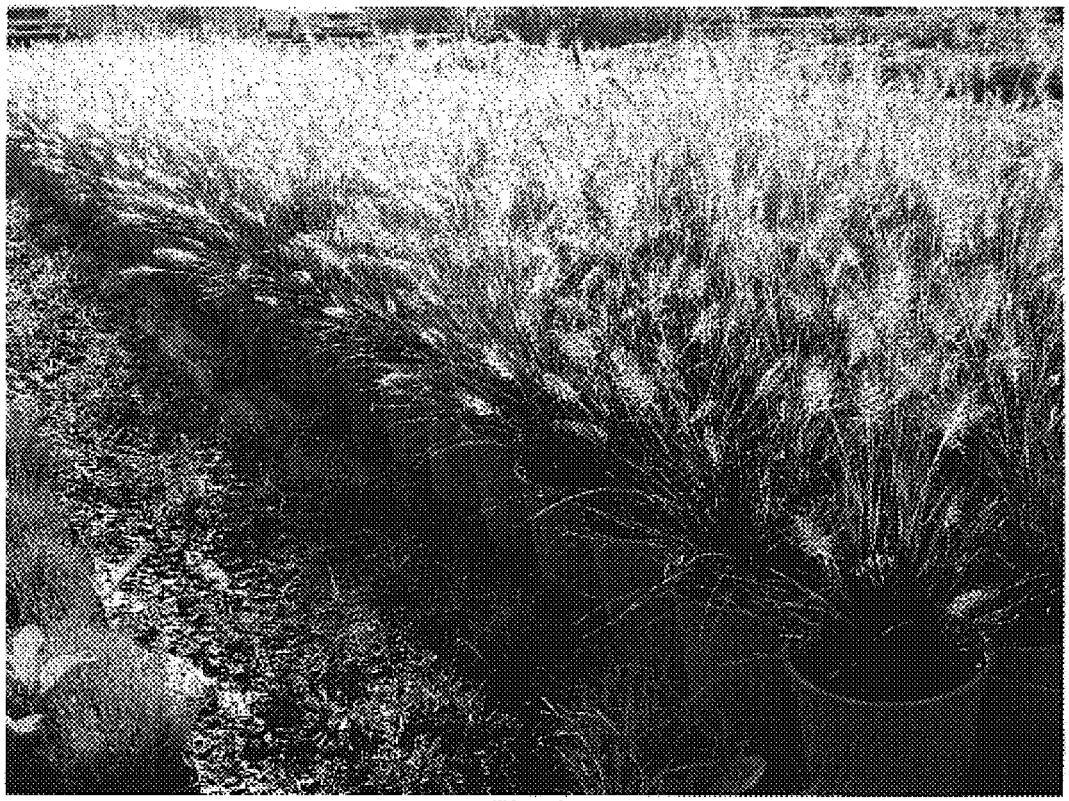
FIG. 2 shows 'Piglet' as potted 1 gallon plants.

In the following description, color references are made to The Royal Horticultural Society Colour Chart. The plant herein described is a one year, one gallon specimen grown in full sun and irrigated in Hebron, Ill.

Botanical classification: *Pennisetum alopecuroides* cultivar 'Piglet'.
Parentage: *Pennisetum alopecuroides* 'Hameln' seedling.
Propagation: Vegetative division.
*Plant description.*—Overall habit of the new *Pennisetum* is strongly clumping mounds with upright stems topped by buff colored flowers in September. Vigor is moderate.
*Plant height.*—40-45 cm.
*Plant width.*—50-60 cm.
*Stem diameter.*—3-4 mm.
Foliage:
*Type.*—Deciduous, grass growing in culms.
*Shape.*—Blade.
*Petiole.*—None.
*Length.*—25 cm.
*Width.*—4 mm.
*Adaxial leaf description.*—The leaf color is green color 146 A.

*Abaxial leaf description.*—The leaf color is green color 146 A.

Flower inflorescence:

*Inflorescence type.*—Terminal bristled spike.

*Inflorescence color.*—As a whole the color is 161 D.

*Individual floret size.*—1-2 mm across, 8-9 mm tall.

*Bristle size.*—1 cm long.

*Overall inflorescence spike size.*—4 cm wide (across), 7-8 cm long (tall).

*Flower number.*—Approximately 60-70 florets per mature spike measuring 4 cm wide (across), 7-8 cm long (tall).

*Fertility.*—Fertile with 3 Anthers and 3 Stamens.

*Blooming habit.*—Terminal bristled spike on up to 60 cm stems.

*Bloom period and duration.*—September into October.

*Scent.*—No scent noticed.

*Bloom color.*—161 D.

*Roots.*—Stiff, fibrous, and freely branching.

*Fruit.*—Seed identical to the species except size.

*Disease resistance.*—Plants are not susceptible to any major pests or diseases.

I claim:

1. A new, distinct *Pennisetum alopecuroides* plant as shown and described, characterized by a short habit of 40-45 cm.

* * * * *